United States Patent
Wright et al.

(10) Patent No.: US 7,114,406 B2
(45) Date of Patent: Oct. 3, 2006

(54) END EFFECTOR INSPECTION APPARATUS AND METHOD

(75) Inventors: Daniel J. Wright, Mercer Island, WA (US); Gary E. Georgeson, Federal Way, WA (US); Michael D. Fogarty, Auburn, WA (US); Stanley W. Richardson, Lake Stevens, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 10/943,045

(22) Filed: Sep. 16, 2004

(65) Prior Publication Data

US 2006/0053907 A1    Mar. 16, 2006

(51) Int. Cl.
    *G01B 5/28* (2006.01)
(52) U.S. Cl. .................................................. 73/866.5
(58) Field of Classification Search .............. 73/866.5, 73/105; 33/559–561, 572; 285/145.1, 121; 248/125.8, 188.5, 326, 333; 403/109.1–109.8
    See application file for complete search history.

(56) References Cited

U.S. PATENT DOCUMENTS

| | | | |
|---|---|---|---|
| 3,585,854 A * | 6/1971 | Hanson et al. ............... 73/105 |
| 3,922,921 A * | 12/1975 | Woo ........................ 73/866.5 |
| 4,167,880 A | 9/1979 | George |
| 4,311,052 A | 1/1982 | Jeffras et al. |
| 4,437,335 A * | 3/1984 | Gates ........................ 73/37.9 |
| 4,491,018 A * | 1/1985 | Stringer et al. ............ 73/865.8 |
| 4,547,119 A | 10/1985 | Chance et al. |
| 5,319,960 A * | 6/1994 | Gamble et al. ............... 73/105 |
| 5,568,954 A * | 10/1996 | Burgess ..................... 292/338 |
| 5,593,633 A | 1/1997 | Dull et al. |
| RE35,510 E * | 5/1997 | McMurtry .................. 33/572 |
| 5,640,811 A * | 6/1997 | Boyle et al. .................. 52/86 |
| 5,902,935 A | 5/1999 | Georgeson et al. |
| 5,954,446 A | 9/1999 | Ireland |
| 6,012,230 A * | 1/2000 | McMurtry et al. ............ 33/559 |
| 6,065,787 A * | 5/2000 | Jarosch ..................... 294/19.1 |
| 6,234,430 B1 * | 5/2001 | Turner, Sr. ............... 248/125.8 |
| 6,484,583 B1 | 11/2002 | Chennell et al. |

(Continued)

FOREIGN PATENT DOCUMENTS

DE    25 19 782 A1    11/1976

(Continued)

OTHER PUBLICATIONS

*Automated Ultrasonic Scanning System (AUSS®), Mobile Automated Scanner (MAUS®)* http://www.engineeringatboeing.com/mfgquality/quality/automatedsystems.html, Jun. 21, 2004, 4 pages.

(Continued)

*Primary Examiner*—Robert Raevis
(74) *Attorney, Agent, or Firm*—Alston & Bird LLP

(57) ABSTRACT

An end effector for inspecting a structure is provided. An end effector includes a magnetically coupled attachment member for connecting the end effector to a control system bridge. An end effector also includes a telescoping arm at least partially disposed inside a tube. A force mechanism provides a force to extend the arm from the tube. A probe attachment, connected to the end of the arm opposite the tube, provides motion in at least one axis relative to the arm for an inspection probe attached to the end effector. Cut-off switches can be used to alert a control system to a separation of the end effector from the bridge and proximity of the bridge to a structure under inspection.

36 Claims, 7 Drawing Sheets

U.S. PATENT DOCUMENTS

| | | | |
|---|---|---|---|
| 6,658,939 | B1 | 12/2003 | Georgeson et al. |
| 6,722,202 | B1 | 4/2004 | Kennedy et al. |
| 6,726,393 | B1 * | 4/2004 | Tsai et al. ............... 403/109.4 |
| 6,748,791 | B1 | 6/2004 | Georgeson et al. |
| 2003/0154801 | A1 | 8/2003 | Georgeson |
| 2003/0210027 | A1 | 11/2003 | Pedigo et al. |
| 2004/0103721 | A1 | 6/2004 | Georgeson |

FOREIGN PATENT DOCUMENTS

| | | |
|---|---|---|
| JP | 04 019086 A | 4/1992 |

OTHER PUBLICATIONS

*Non Destructive Testing*, http://www.aascworld.com/ndt-ttu.htm, Aug. 19, 2004, 3 pages.

*Inspection of In-Service Composite-Honeycomb Structures,* Aerospace Application Note, Rev.: Jan. 2002, R/D Tech.

*Probe Catalog 2003-2004,* Thru-Transmission Ultrasonics, NDT Engineering Corporation, R/D Tech Company, pp. 1-11.

*Air-Coupled Ultrasonic Inspection,* http://www.qmi-inc.com/AIRSCAN.htm, Aug. 19, 2004, 3 pages.

*AIRSCAN® Transducer Specifications,* http://www.qmi-inc.com/Airscan%20TX%20Specifications.htm, Aug. 19, 2004, 18 pages.

U.S. Appl. No. 10/752,890, filed Jan. 7, 2004, In re: Bossi et al., entitled *Non-Destructive inspection Device for Inspecting Limited-Access Features of a Structure.*

U.S. Appl. No. 10/734,452, filed Dec. 12, 2003, In re: Bossi et al., entitled *Ultrasonic Inspection Device for Inspecting Components at Preset Angles.*

* cited by examiner

END EFFECTOR INSPECTION APPARATUS AND METHOD

CROSS-REFERENCE TO RELATED APPLICATIONS

The contents of co-pending applications filed concurrently herewith and entitled "Magnetically Attracted Inspecting Apparatus and Method Using a Fluid Bearing," "Magnetically Attracted Inspecting Apparatus and Method Using a Ball Bearing," "Alignment Compensator for Magnetically Attracted Inspecting Apparatus and Method," and "Apparatus and Method for Area Limited-Access Through Transmission Ultrasonic Inspection" are incorporated by reference in their entireties. The contents of U.S. Pat. No. 6,722,202 to Kennedy are incorporated by reference in its entirety.

FIELD OF THE INVENTION

The present invention relates generally to an apparatus and method for inspecting a structure and, more particularly, to an apparatus and method for connecting an inspection probe to a control system.

BACKGROUND

Structures are commonly inspected for any type of internal or external damage to or flaws in the structure. For example, inspection may be required to validate the integrity and fitness of a structure for continued use in manufacturing and future ongoing use in-service. A typical inspection method is non-destructive inspection (NDI) which involves thoroughly examining a structure without harming the structure or requiring significant disassembly of a product including the structure. Among the structures that are routinely tested are composite structures, such as composite sandwich structures and other adhesive bonded panels and assemblies. In this regard, composite structures are commonly used throughout the aircraft industry because of the engineering qualities, design flexibility and low weight of composite structures, such as the stiffness-to-weight ratio of a composite sandwich structure. For example, composite structures are used to fabricate parts for F-22 aircraft. As such, it is frequently desirable to inspect composite structures to identify any flaws, such as cracks, voids or porosity, which could adversely affect the performance of the composite structure. For example, typical flaws in composite sandwich structures, generally made of one or more layers of lightweight honeycomb or foam core material with composite or metal skins bonded to each side of the core, include disbonds which occur at the interfaces between the core and the skin or between the core and a septum intermediate skin.

Non-destructive inspection may be performed using a variety of methods, including pulse-echo (PE), through transmission (TT), or shear wave inspection techniques to obtain data, such as for thickness gauging, detection of laminar defects and porosity, and/or crack detection in the structure. Resonance, pulse echo or mechanical impedance sensors may be used to provide indications of voids or porosity, such as in adhesive bondlines of the structure. High resolution inspection of aircraft structure are commonly performed using semi-automated ultrasonic testing (UT) to provide a plan view image of the part or structure under inspection. While solid laminates may be inspected using one-sided pulse echo ultrasonic (PEU) testing, composite sandwich structures typically require through-transmission ultrasonic (TTU) testing for high resolution inspection. In through-transmission ultrasonic inspection, ultrasonic sensors such as transducers, or a transducer and a receiver sensor, are positioned facing the other but contacting opposite sides of the structure to be inspected such as opposite surfaces of a composite material. An ultrasonic signal is transmitted by at least one of the transducers, propagated through the structure, and received by the other transducer. Data acquired by sensors, such as TTU transducers, is typically processed by a processing element, and the processed data may be presented to a user via a display.

Non-destructive inspection may be performed manually by technicians who typically move an appropriate sensor over the structure. Manual scanning generally consists of a trained technician holding a sensor and moving the sensor along the structure to ensure the sensor is capable of testing all desired portions of the structure. In many situations, the technician must repeatedly move the sensor side-to-side in one direction while simultaneously indexing the sensor in another direction. For a technician standing beside a structure, the technician may repeatedly move the sensor right and left, and back again, while indexing the sensor between each pass. In addition, because the sensors typically do not associate location information with the acquired data, the same technician who is manually scanning the structure must also watch the sensor display while scanning the structure to determine where the defects, if any, are located in the structure. The quality of the inspection, therefore, depends in large part upon the technician's performance, not only regarding the motion of the sensor, but also the attentiveness of the technician in interpreting the displayed data. Thus, manual scanning of structures is time-consuming, labor-intensive, and prone to human error.

Semi-automated inspection systems have been developed to overcome some of the shortcomings with manual inspection techniques. For example, the Mobile Automated Scanner (MAUS®) system is a mobile scanning system that generally employs a fixed frame and one or more automated scanning heads typically adapted for ultrasonic inspection. A MAUS system, such as a MAUS-V system, may be used with pulse-echo, shear wave, and through-transmission sensors. The fixed frame may be attached to a surface of a structure to be inspected by vacuum suction cups, magnets, or like affixation methods. Smaller MAUS systems may be portable units manually moved over the surface of a structure by a technician. However, for through-transmission ultrasonic inspection, a semi-automated inspection system requires access to both sides or surfaces of a structure which, at least in some circumstances, will be problematic, if not impossible, particularly for semi-automated systems that use a fixed frame for control of automated scan heads.

Automated inspection systems have also been developed to overcome the myriad of shortcomings with manual inspection techniques. For example, the Automated Ultrasonic Scanning System (AUSS®)) system is a complex mechanical scanning system that employs through-transmission ultrasonic inspection. The AUSS system can also perform pulse echo inspections, and simultaneous dual frequency inspections. The AUSS system has robotically controlled probe arms that must be positioned proximate the opposed surfaces of the structure undergoing inspection with one probe arm moving an ultrasonic transmitter along one surface of the structure, and the other probe arm correspondingly moving an ultrasonic receiver along the opposed surface of the structure. To maintain the ultrasonic transmitter and receiver in proper alignment and spacing with one another and with the structure undergoing inspection, the AUSS-X system has a complex positioning system that provides motion control in ten axes.

One difficulty when using control systems is the connection between the control system and the inspection probe. Typically, control arms and direct attachments are used to connect a probe to a control system. Unfortunately, however, using a control arm or directly attaching a control system to a probe brings the control system into proximity with the structure under inspection. The proximity of the control system to the structure can lead to damage to the control system and the part such as instances where the control system impacts the structure.

Accordingly, a need exists for an improved non-destructive inspection device and method to inspect a structure.

SUMMARY OF THE INVENTION

An end effector inspection apparatus and method are provided according to various embodiments of the present invention. An end effector is used to connect a control system to an inspection probe. An end effector also provides separation between the control system and the inspection probe to decrease the chance of damage to either the control system or the structure. An end effector may be used for manual, semi-automated, and automated inspection of a structure, but is especially useful for connecting an inspection probe to a semi-automated or automated control system. An end effector may also provide such features as safety cut-off switches, magnet release clamps, alignment members and alignment indentations for orientation and alignment for attachment, clamping tube mounts, a detachable extension tube, and a retracted locking position and such functions as quick release from a control system to prevent damage.

An end effector according to one embodiment of the present invention includes a telescoping arm, a tube, a force mechanism, and a magnetically coupled attachment member. The telescoping arm is at least partially disposed within the tube. The force mechanism is coupled to the arm and the tube to exert a force to extend the arm from the tube. The magnetically coupled attachment member connects to the tube and may include at least one releasable clamp for connecting to the tube. The releasable clamp may allow for positioning of the tube with respect to the attachment member, such as to slide the tube in one direction relative to the attachment member. A detachable extension tube may be attached to the primary tube for increasing the length of the telescoping arm relative to the position of the attachment member. The attachment member may include a cut-off switch to indicate when the attachment member is not connected to a support mechanism such as a control system bridge. The attachment member may include alignment members which are used when attaching the attachment member to a support mechanism such as a control system bridge. The attachment member may also include a magnetic coupling offset release clamp for releasing the magnetic attraction between the attachment member and a support mechanism such as for attaching or disengaging the attachment member from the support mechanism.

The arm or the tube may include a cut-off switch to indicate when the arm is retracted into the tube beyond the predefined amount of retraction. Typically, the arm is rotatably fixed with respect to the tube such that the arm does not rotate within the tube. Corresponding grooves and ridges in and on the arm and tube may prevent rotation of the arm within the tube. An indentation or dent around a portion of the arm or within a portion of the tube and a corresponding bump inside the tube or around the arm may fix the arm within the tube in a retracted position where the bump extends into the tube. A bump may include at least one depressible ball which may extend into the dent. The cut-off switch on the arm or tube may indicate when the arm is retracted into the tube beyond the interface of the dent and the bump.

A force mechanism between a tube and an arm may be, for example, a retractable metal spring, a compressible spring, or a piston. Bearings may be included to support the arm in the tube. The arm rides on the bearings within the tube in order to extend from and retract into the tube. A probe attachment may be coupled to the distal end of the arm from the tube and provide at least one axis of motion relative to the arm. A second-axis rotor may be connected between the tube and attachment member in order to provide at least one additional axis of rotation for the tube relative to the attachment member.

According to another aspect of the present invention, an apparatus for inspecting a structure includes an end effector with a telescoping arm, a tube, a magnetically coupled attachment member, and an inspection probe connected to the distal end of the arm from the tube. The apparatus for inspecting a structure may also include a control system comprising a bridge magnetically coupled to the attachment member of the end effector. The attachment member may include alignment members inserted into corresponding indentations in the bridge. The alignment members in the corresponding indentations are used for positioning the attachment member with respect to the bridge for magnetic coupling. The attachment member may include a magnetic coupling offset release clamp for releasing the magnetic attraction or preventing the full magnetic attraction of the coupling between the attachment member and the bridge. For example, the magnetic coupling offset release clamp may include an extension which protrudes from the attachment member between the attachment member and the bridge for providing separation between the bridge and the attachment member. The bridge or the attachment member may include a cut-off switch for indicating when the bridge and the attachment member are connected and/or separated. The end effector may also include a probe attachment coupled to the distal end of the arm from the tube for connecting the end effector to the inspection probe.

According to yet another aspect of the present invention, a method of inspecting a structure is provided. The method includes the steps of magnetically coupling a control system to an attachment member of an end effector, coupling an inspection probe to the end effector, positioning an inspection probe against the surface of a structure, and controlling inspection of the structure with the control system. The step of positioning the inspection probe may include the step of telescoping an arm of the end effector to permit the inspection probe to contact the surface of the structure. The step of telescoping the arm of the end effector may include the step of exerting a force upon the arm of the end effector to extend the arm from the tube. The method may also include the step of releasing the magnetic coupling of the bridge and the attachment member by separating the bridge and the attachment member. The separation of the bridge and the attachment member may be performed by protruding an extension from at least one of the bridge and the attachment member between the bridge and the attachment member.

These and other characteristics, as well as additional details, of the present invention are further described in the Detailed Description with reference to these and other embodiments.

BRIEF DESCRIPTION OF THE DRAWING(S)

Having thus described the invention in general terms, reference will now be made to the accompanying drawings, which are not necessarily drawn to scale, and wherein:

DETAILED DESCRIPTION

The present invention will be described more fully with reference to the accompanying drawings. Some, but not all, embodiments of the invention are shown. The invention may be embodied in many different forms and should not be construed as limited to the embodiments described. Like numbers and variables refer to like elements and parameters throughout the drawings.

An end effector of the present invention can be used to connect a control system, such as a control bridge of an AUSS-X to an inspection probe. An end effector may advantageously be used with magnetically coupled inspection probes which do not require multi-axis robotic systems. Rather, magnetically coupled inspection probes only require one of the probes to be driven over a surface of the structure under inspection. An end effector operably engages the inspection probe and translates a force from the control system for moving the probe across a surface of a structure. At the same time, an end effector permits the probe to rotate and extend to follow the contour of the surface of the structure. For example, an end effector may be connected to the probe using a rotatable knuckle attachment which provides for on-axis rotation; off-axis rotation, also referred to as bending or hinging; and linear extension of the probe to permit the probe to follow the contour of the surface of the structure in any direction of movement over the surface while maintaining magnetic coupling with a probe on an opposing surface of the structure. An end effector is used to permit an inspection probe to contact, and maintain contact with, the structure. Accordingly, an end effector permits contour-following for magnetically coupled scanning of large, contoured structures. For example, an end effector may be used for non-destructive PE and TTU inspection of a composite payload fairing such as for low frequency ultrasonic bond inspection and eddy current testing.

Figure 1:
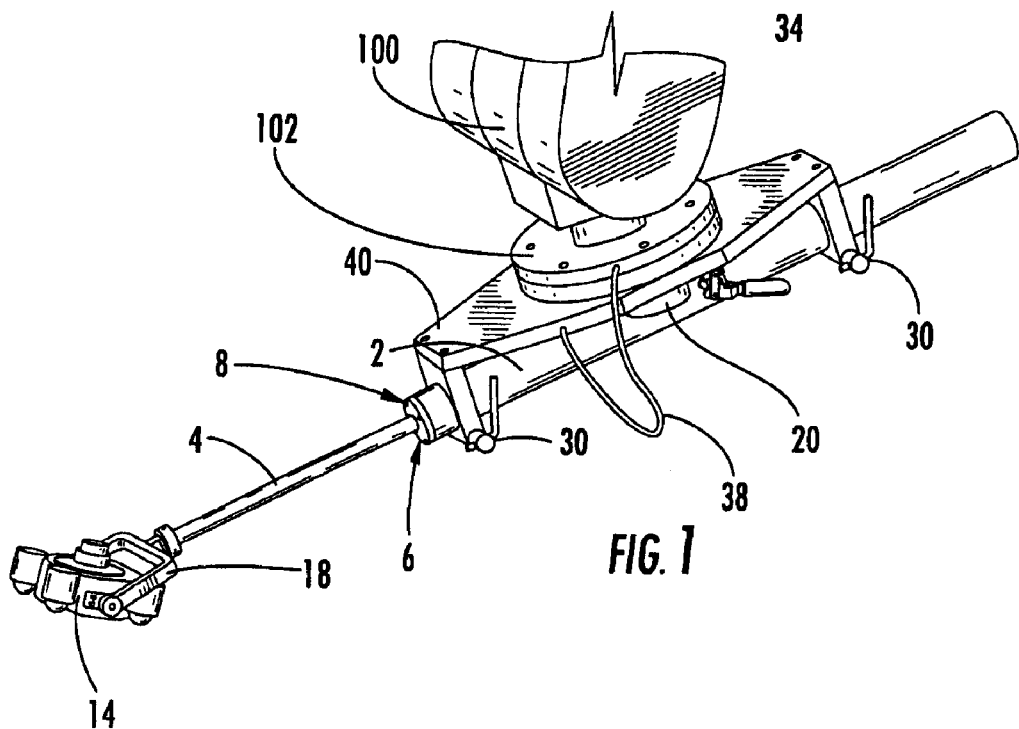
FIG. 1 is a side perspective view of an end effector connecting a control bridge to an inspection probe according to an embodiment of the present invention.
Figure 2:
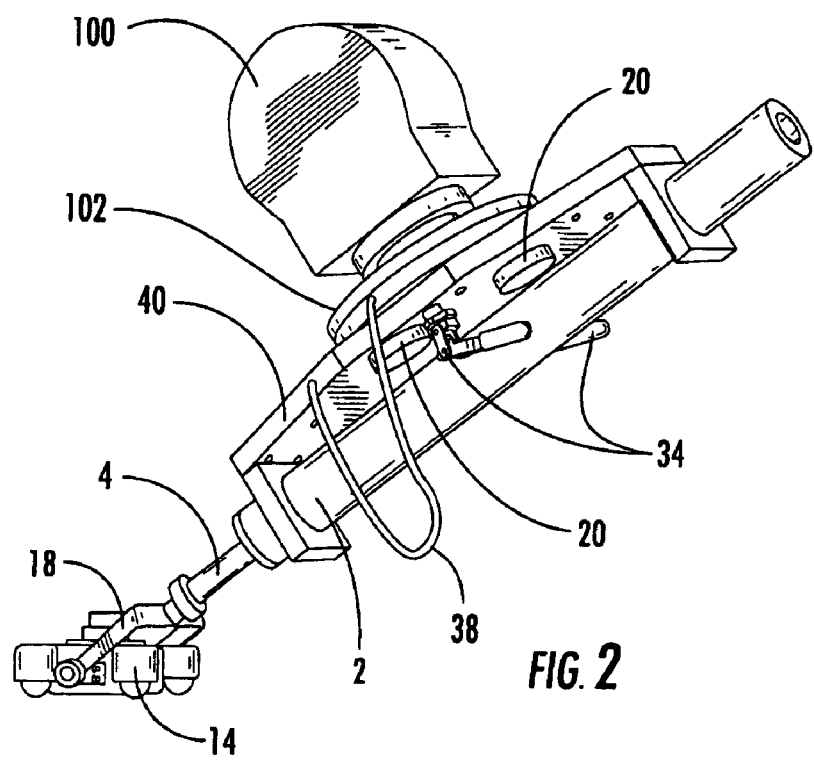
FIG. 2 is a bottom perspective view of the end effector connecting a control bridge to an inspection probe according to an embodiment of the present invention.

FIG. 1 is a side perspective view of an end effector connecting a control bridge to an inspection probe according to an embodiment of the present invention. FIG. 2 is a bottom perspective view of the end effector. Typically, an end effector is used to attach an inspection probe 14 to the base 102 of a bridge 100 of a control system. The bridge 100 of the control system is used to control an inspection probe 14, such as moving the probe 14 back and forth over a structure under inspection. An end effector includes a telescoping arm 4 inside a tube 2 such as a larger hollow sleeve. For example, the arm 4 may slide on internal bearings inside the hollow tube 2 to permit extension and retraction of the arm 4, such as the ball and socket bearings 294 shown in FIG. 1C. The arm 4 may freely extend and retract in order to permit the magnetically coupled inspection probe 14 to contact the structure under inspection and follow contours of a surface of the structure without requiring the control system bridge 100 to be precisely programmed for the contours of the surface of the structure. For example, the bridge 100 of a control system using an end effector with a two foot telescoping arm 4 would only need to keep within approximately two feet of proximity of the structure. The telescoping arm 4 and the multi-axis rotation of the magnetically coupled inspection probe 14 provide the difference between the rough positioning of the control system bridge 100 and the contours of the surface of the structure. Typically an arm and a tube are cylindrical with circular cross-sectional circumferences. However, an arm and a tube may be formed with corresponding non-circular cross-sectional shapes, such as an ellipse or hexagon cross-sectional shape. Additional corresponding, non-circular cross-sectional shapes for an arm and a tube include, for example, regular polygons, including triangles, squares, rectangles, octagons, and the like and irregular polygons, shapes, configurations, and combinations.

An end effector typically includes a force mechanism to provide a constant outward force to extend the arm 4. An outward force helps to ensure that the end effector does not unintentionally pull the inspection probe 14 off the structure under inspection, but instead helps to keep the inspection probe 14 against the structure. A force mechanism is preferably adapted to provide a constant outward force while permitting the telescoping arm 4 to easily retract into the hollow tube 2.

An end effector of the present invention may be used for manual, semi-automated, and automated inspection of a structure, but is especially useful for connecting an inspection probe to a semi-automated or automated control system. An example of a semi-automated control system which can be used with an embodiment of the present invention is a robotic gantry scanning system manufactured by CIMCORP Precisions Systems, Inc., of Ulvila, Finland, a part of which is now PAR Systems, Inc., of Shoreview, Minn., with a CIMROC®2 controller and an XR6050 bridge manufactured by GCA, Inc., and using ScanMaster™ control software by ScanMaster Systems (IRT) Ltd. (formerly IRT) of Hod Ha'Sharon, Israel, and IRT ScanMaster Systems, Inc., of Nashua, N.H.

The end effector is attached to the base 102 of the bridge 100 of the control system with an attachment member 40.

Magnetic coupling is used to attach the end effector to the control system. For example, magnets 20 on the attachment member 40 may be magnetically attracted to the bridge base 102 constructed of stainless steel or other ferromagnetic material. Various other magnetic coupling mechanisms may be used. For example, the magnets and the ferromagnetic elements may be interchanged. Two magnets may be used. "Magnet" includes permanent magnets and electromagnets. To assist in attachment of the end effector to the control system, an attachment member 40 may include offset release clamps 34 that are used to provide a separation to decouple the end effector from the control system, such as decreasing the magnetic attraction of the magnets 20 of the attachment member 40 to the bridge base 102 by separating the magnets 20 from the bridge base 102.

The magnetic coupling allows the end effector to safely break away from the control system, such as if the end effector or probe collides with a portion of the structure under inspection. The magnetic coupling may also permit the end effector to rotate with respect to the control system bridge 100 in the case of a collision, such as where the magnetic coupling is strong enough to keep the end effector and the control system attached but where alignment members 50 of the attachment member 40 of the end effector are disengaged from corresponding indentations 52, 53 in the control system bridge 100. By comparison to current systems which do not separate or may break apart such as using plastic screws to permit separation of an inspection probe from a control bridge, magnetic coupling may be quickly and easily reattached and is easily adjusted such as using different magnets to control the strength of a force that can separate an end effector from a control bridge. Accordingly, in accordance with embodiments of the present invention, the magnetic coupling between an end effector and a control system is a force strong enough to retain the end effector in a fixed position relative to the control system but weak enough to permit the end effector to break away from or rotate with respect to the control system due to a sufficient amount of force directed against the end effector, such as a predetermined force perpendicular to the motion of the end effector. Similarly, in accordance with embodiments of the present invention, the force of the magnetic coupling should be weak enough to permit manual separation of the end effector from the control system, such as using offset release clamps 34.

A probe attachment 18 may be affixed to the end of the arm 4 opposite the tube 2 in order to hold an inspection probe 14. A probe attachment 18 may provide for multi-axis rotation of the inspection probe 14 with respect to the arm 4 and thereby the end effector and control system. For example, a probe attachment 18 may be a yoke attachment affixed to opposing sides of an inspection probe 14 with rotatable hinges attached to the inspection probe 14 and a rotatable and/or hinged attachment to the arm 4.

An end effector may include additional features such as quick release clamps 30 which are used to position a tube 2 of the end effector with respect to the attachment member 40. Quick release clamps 30 may be used to conveniently increase or decrease the reach of the control system using the end effector to position an inspection probe 14 against a structure under inspection. The quick release clamps 30 hold the magnets 20 off the bridge base 102 to allow easy attachment and detachment of the end effector to and from the control system bridge 100. An example quick release clamp is a clamp which permits manual releasing and securing of the clamp, such as and/or similar to bicycle quick release skewers that use levered cams to exert a clamping force on a skewer. An end effector may also include offset release clamps 34 that allow an operator to align the end effector, specifically the attachment member 40 of the end effector, as it is attached to a control system bridge 100. Offset release clamps 34 also allow an operator to easily remove an end effector from a control system bridge 100, such as when scanning is complete or to perform other types of scanning. An offset release clamp is a clamp which permits manual adjustment of an extension for separating a magnetic coupling between a control system and an end effector and/or holding apart a partial magnetic coupling during attachment or adjustment of a control system and an end effector, such as a levered cam which translates a rotational force to a linear force. Typically, an offset release clamp would provide at least two fixed positions, such as an open position to separate or hold apart a control system and an end effector and a closed position when a control system and an end effector are attached.

Figure 1A:
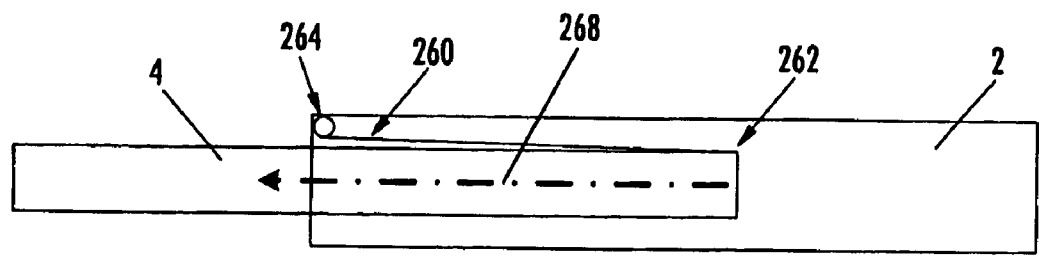
FIG. 1A is a schematic diagram of a retractable metal spring force mechanism for an end effector according to an embodiment of the present invention.
Figure 1B:
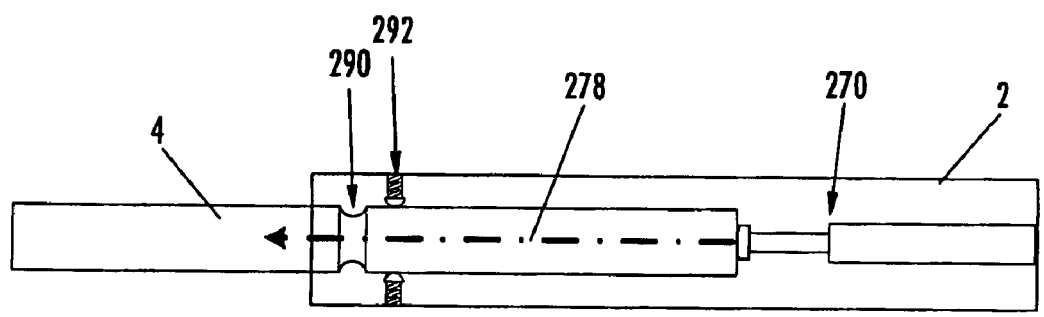
FIG. 1B is a schematic diagram of a piston force mechanism for an end effector according to an embodiment of the present invention.
Figure 1C:
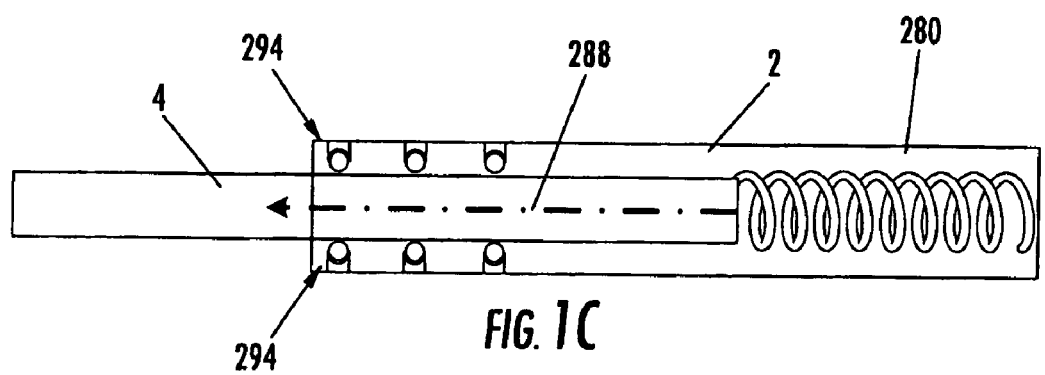
FIG. 1C is a schematic diagram of a compressible spring force mechanism for an end effector according to an embodiment of the present invention.
Figure 3:
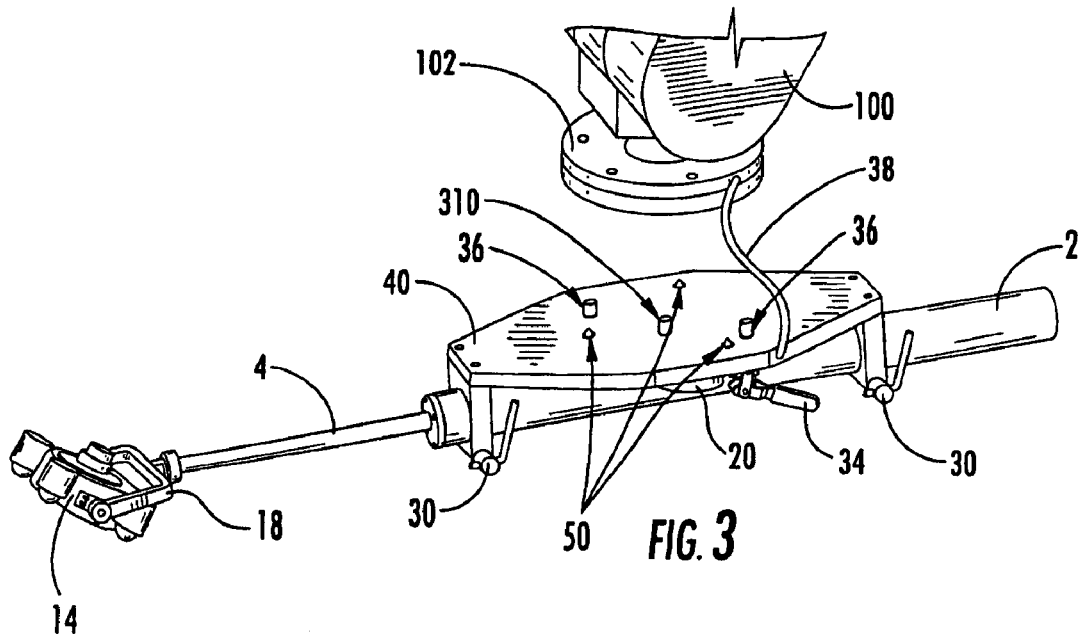
FIG. 3 is a side perspective view of a connection between an end effector and a control bridge according to an embodiment of the present invention.

A force mechanism is included in the end effector to provide an outward force to extend the arm 4 from the tube 2, such as the outward forces 268, 278, 288 of FIGS. 1A, 1B, and 1C. As shown in FIG. 1A, an example force mechanism may be a retractable metal spring 260 attached to the end 262 of the arm 4 inside the tube 2 and the end 264 of the tube 2 through which the arm 4 extends. Another example force mechanism is a compressible spring 270 as shown in FIG. 1C. Yet another example force mechanism is a piston 280 as shown in FIG. 1B, such as a gas piston, to press on and drive the arm 4 out of the tube 2. Other types of force mechanisms may be used to provide an outward force for the telescoping arm 4. Preferably, the force mechanism provides a constant outward force which is sufficient to extend the arm 4 and the inspection probe 14 for positioning and holding the inspection probe 14 against a surface of the structure under inspection.

Typically, the arm of an end effector of the present invention is rotatably fixed with respect to the tube such that the arm does not rotate within the tube to permit the control system to know and/or determine the orientation of a probe on the surface of a structure. Corresponding grooves and ridges in and on the arm and tube, such as flats, splines, or keys, may prevent rotation of the arm within the tube. For example, an arm may include indentations or grooves along a portion of the length of the arm which correspond to extensions or ridges on the inside circumference of a tube. Alternatively, or in addition, an arm and a tube may be formed with corresponding non-circular shapes, such as an ellipse or hexagon cross-sectional shapes, to prevent the arm from rotating with the tube while permitting the arm to extend from and retract within the tube. Additional corresponding, non-circular cross-sectional shapes include, for example, regular polygons and irregular polygons as described further above.

An end effector may be adapted to provide a releasable latch for fixed retraction of the arm 4 within the tube 2. For example, as shown in FIG. 1B, the arm 4 may include a dent 290 around at least a portion of the circumference of the arm 4, such as proximate the distal end of the arm 4 from the tube 2. The tube 2 may then include a bump 292, such as depressible balls, which extends into the dent of the arm 4, thus creating a releaseable latch. The ball and dent latch stop position 6 would preferably hold the arm 4 in a fixed, retracted position in the tube 2 to overcome the outward force of the force mechanism such as to allow for movement of a control system bridge with an attached end effector and inspection probe before, during, or after scanning a structure.

A cut-off switch 8 may be used to provide information as to when the arm 4 may be retracted into the tube beyond a predefined location. The cut-off switch 8 signals when it is tripped. For example, if the arm 4 extends past the ball and dent latch stop position 6 within the tube, the cut-off switch 8 may be activated to indicate that the control system bridge 100 is too close to the structure under inspection. A cut-off switch for an embodiment of the present invention may include a depressible switch, a radio frequency chip, an optical sensor, a linear wheel, or other mechanism to indicate a position, attachment, or separation. For example, an attachment member 40 may include a depressible switch to indicate attachment and/or separation, and a tube 2 may include an optical sensor to indicate when the arm 4 passes a predefined retracted position.

Figure 4:
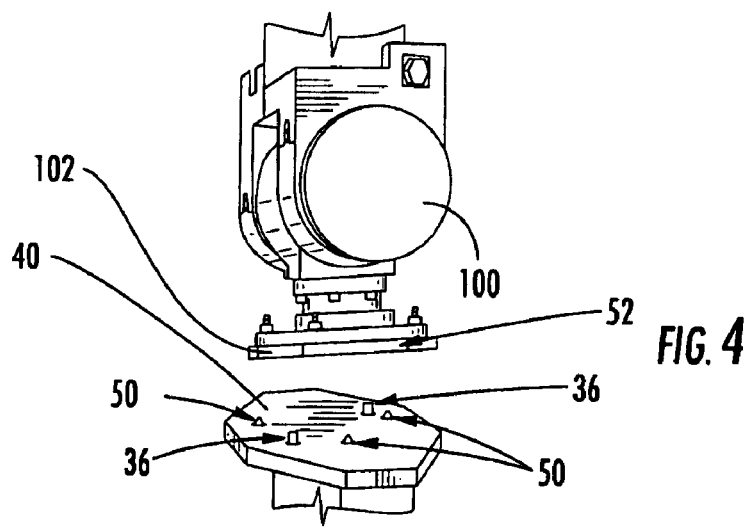
FIG. 4 is an orthogonal side perspective view of the connection between the end effector and the control bridge.
Figure 4A:
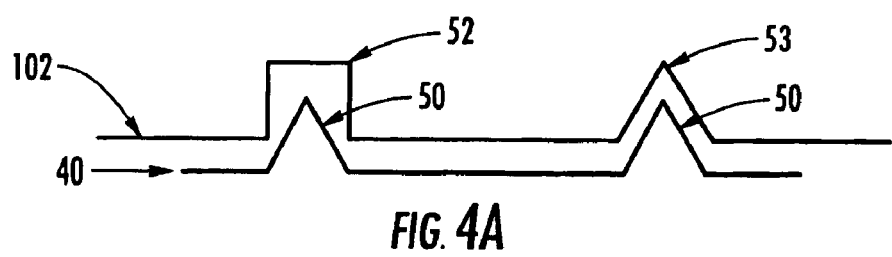
FIG. 4A is a schematic diagram of alignment members and bridge base indentations according to an embodiment of the present invention.
Figure 5:
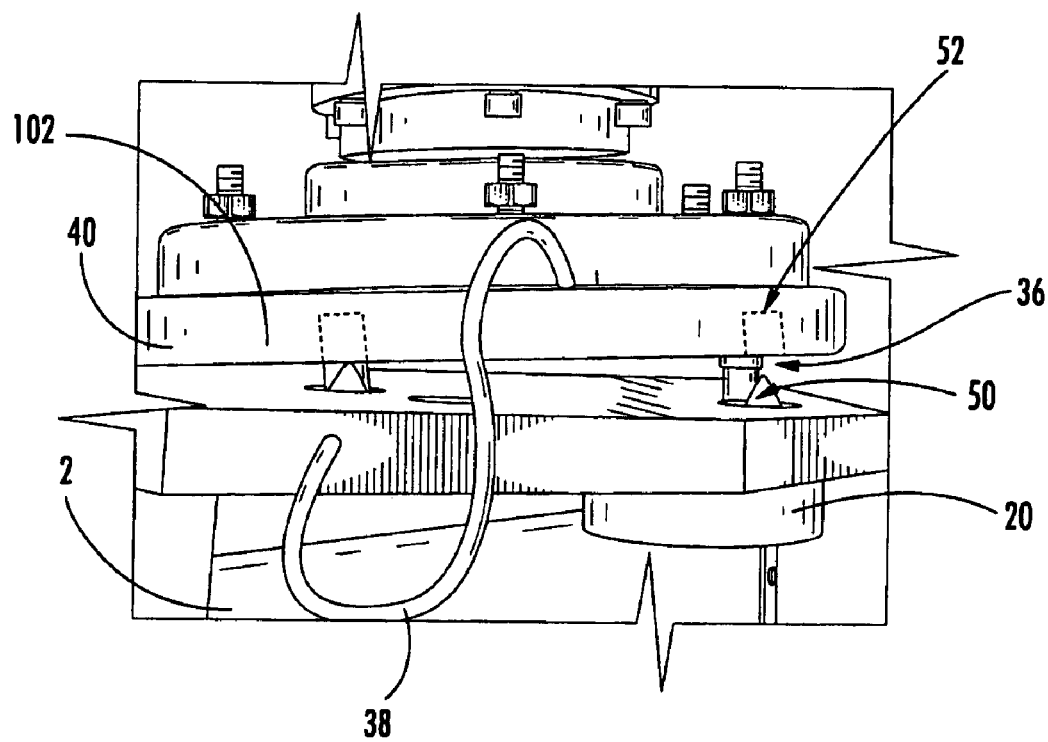
FIG. 5 is a side view of the connection between the end effector and the control bridge.

The attachment member 40 includes alignment members 50 which correspond to indentations 52, 53 in the bridge base 102 which are positioned to provide for a predetermined orientation and alignment of the end effector with respect to the control system bridge 100. Alignment members 50 may be inverted conical extensions from the attachment member 40 which fit within cylindrical indentations 52 or conical indentations 53 in the bridge base 102. By using inverted conical alignment members 50, the alignment members 50 may be off-set or misaligned from the corresponding indentations in the bridge base 102 and provide for proper alignment and orientation of the end effector with respect to the control system bridge 100 as the alignment members 50 are pulled into the indentations 52, 53 in the bridge base 102 by the magnetic coupling between the attachment member 40 and the control system bridge 100. For example, the magnets 20 of the attachment member 40 pulled the alignment members 50 up and into the indentations of the stainless steel bridge base 102. For example, FIG. 4A shows alignment members 50 extending into corresponding bridge indentations 52, 53. The alignment member 50 may be sized such that when the attachment member 40 is adjacent to the bridge base 102, the bridge indentations 52, 53 hold the alignment members 50 in a central position relative to the bridge indentations 52, 53. Alignment members and alignment indentations may be other geometric and structural shapes which provide for orientation and alignment of an attachment member and a control system bridge. An extension 36 of an offset release clamp 34 may provide for separation between the bridge base 102 and the attachment member 40 for positioning the alignment members 50 with respect to the bridge indentations 52, 53. An extension 36 of an offset release clamp 34 also provides separation of the bridge base 102 and the attachment member 40 in order to reduce the magnetic attraction between the magnet 20 and the bridge base 102 to permit attachment and removal of the end effector to the control system in addition to the orientation of the end effector with respect to the control system bridge 100 for affixing the end effector to the control system. Other shapes, sizes, and types of extensions from or indentations in the attachment member and corresponding indentations or extensions in the control system bridge 100 or bridge base 102 may be used to orient in position an end effector with respect to a control system bridge 100 in accordance with embodiments of the present invention.

A cut-off switch 310 may be positioned in the center of the attachment member 40, or at another location, in order to provide information as to when the attachment member 40 and the control system bridge 100 are affixed or separated. For example, the cut-off switch 310 may be depressed by the bridge base 102 when the end effector is magnetically coupled to the bridge base 102 by the magnets 20 of the attachment member 40. When the end effector is separated from the control system bridge 100, the cut-off switch is no longer depressed and may indicate that the end effector has separated from the control system bridge 100. For example, a cut-off switch 310 providing information that an end effector has separated from a control system bridge 100 may indicate to turn off the power to the control system bridge 100 or, more particularly, to stop motion of the control system bridge 100 to prevent a collision between the control system bridge 100 and the structure under inspection, or further damage to the control system bridge 100 and/or of the structure under inspection. A cut-off switch 310 may be positioned in other areas of the attachment member 40 or on the control system bridge 100 or bridge base 102 such that the cut-off switch provides information as to when the end effector and control system bridge are affixed or detached in accordance with embodiments of the present invention.

An end effector can separate from the control system bridge. If a force on the end effector overcomes the attractive force of the magnetic coupling between the attachment member 40 and the control system bridge 100 or bridge base 102, the end effector will pull away or separate from the control system bridge 100 or bridge base 102. To prevent the end effector from falling away from the control system bridge 100 and impacting the structure, a loose connector 38 may be used between the end effector and the control system bridge 100, such as an elastic connection which permits the end effector to separate from the control system bridge 100 but prevents the end effector from falling to the structure under inspection. For example, if the control system bridge is generally separated from a structure under inspection using an end effector by approximately two feet, a connector 38, such as an elastic connection, can provide for one foot of separation of the end effector from the control system bridge 100. Thus, if a force such as a collision of the end effector with the structure under inspection, causing the end effector to separate from the control system bridge 100, the connector 38 may prevent the end effector from completely falling and impacting the structure under inspection. But by allowing the end effector to separate from the control system bridge 100, damage or further damage to the control system bridge 100 and/or the structure under inspection may be prevented.

Figure 6:
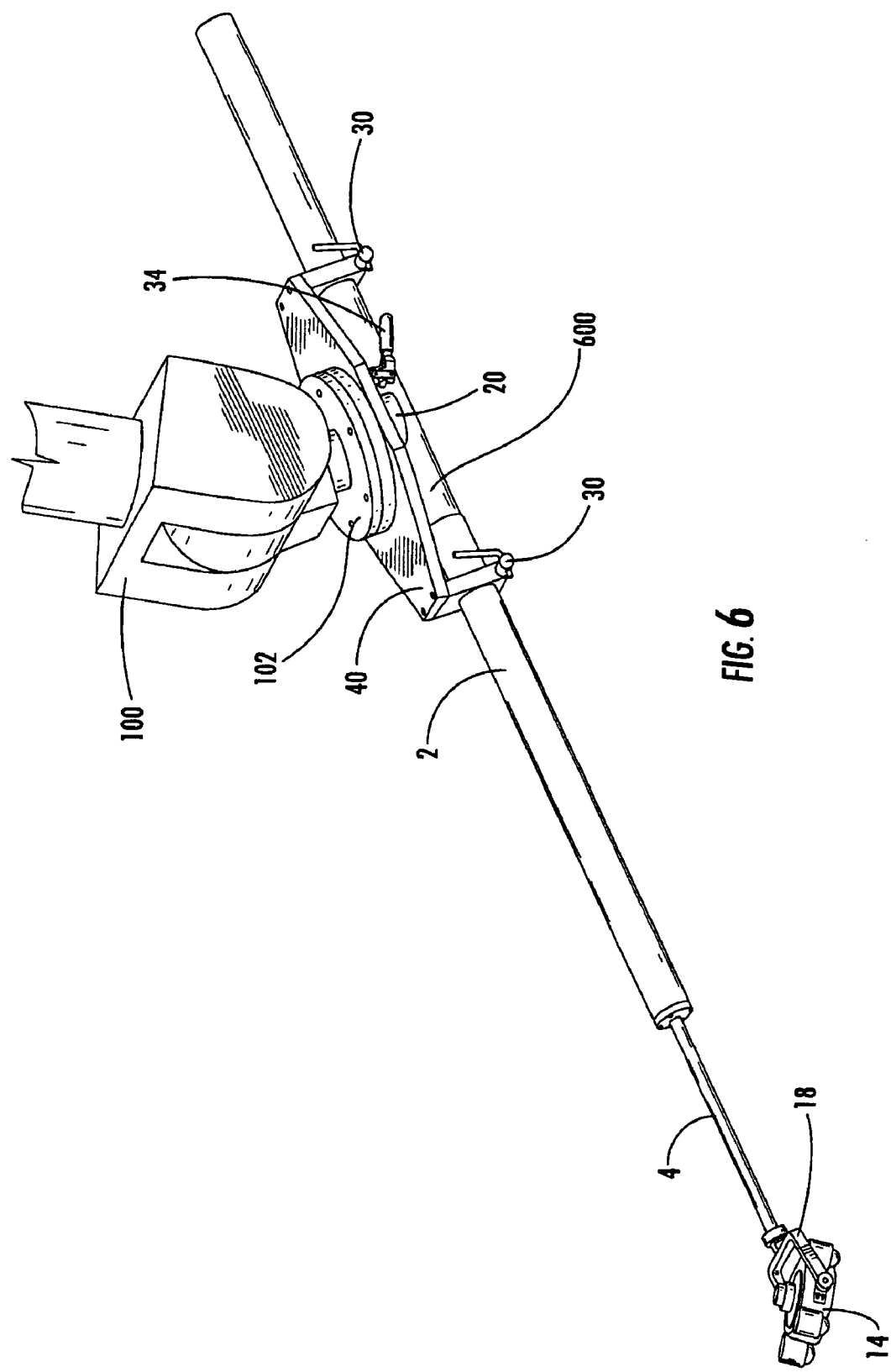
FIG. 6 is a side perspective view of an end effector with a tube extension connecting a control bridge to an inspection probe according to an embodiment of the present invention.

FIG. 6 is a side perspective view of an end effector with a tube extension connecting a control bridge to an inspection probe according to an embodiment of the present invention. A tube extension 600 may be affixed to the tube 2 of an end effector in order to provide additional length of the arm 4 for positioning and holding an inspection probe 14 against a surface of a structure under inspection. The tube extension 600 also provides additional separation between the structure under inspection and the control system bridge 100. An extension 600 of an end effector tube 2 may be a second tube, rod, or other cylindrical structure having the same outer circumference shape and diameter as the end effector tube. The extension 600 may be detachable, such as by threading the ends of the tube 2 and the extension 600 together using a threaded rod which screws into a portion of the tube 2 and the extension 600. Using quick release clamps 30, the tube 2 and tube extension 600 may be positioned with respect to the control system bridge 100 by sliding the tube 2 and extension 600 with respect to the attachment member 40. Using an end effector of the present invention, and particularly an end effector with a tube extension 600, allows a control system to inspect larger, more complex structures such as inspecting a portion of a Sea Launch payload fairing. A tube extension 600 provides an end effector the ability to extend substantial distances away from a control system bridge 100. End effectors of a present invention may also decrease the cost of inspection of a structure by using an end effector of the present invention which permits inspection of large, complex structures rather than requiring the use of costly multi-arm, multi-axis control systems.

Figure 7:
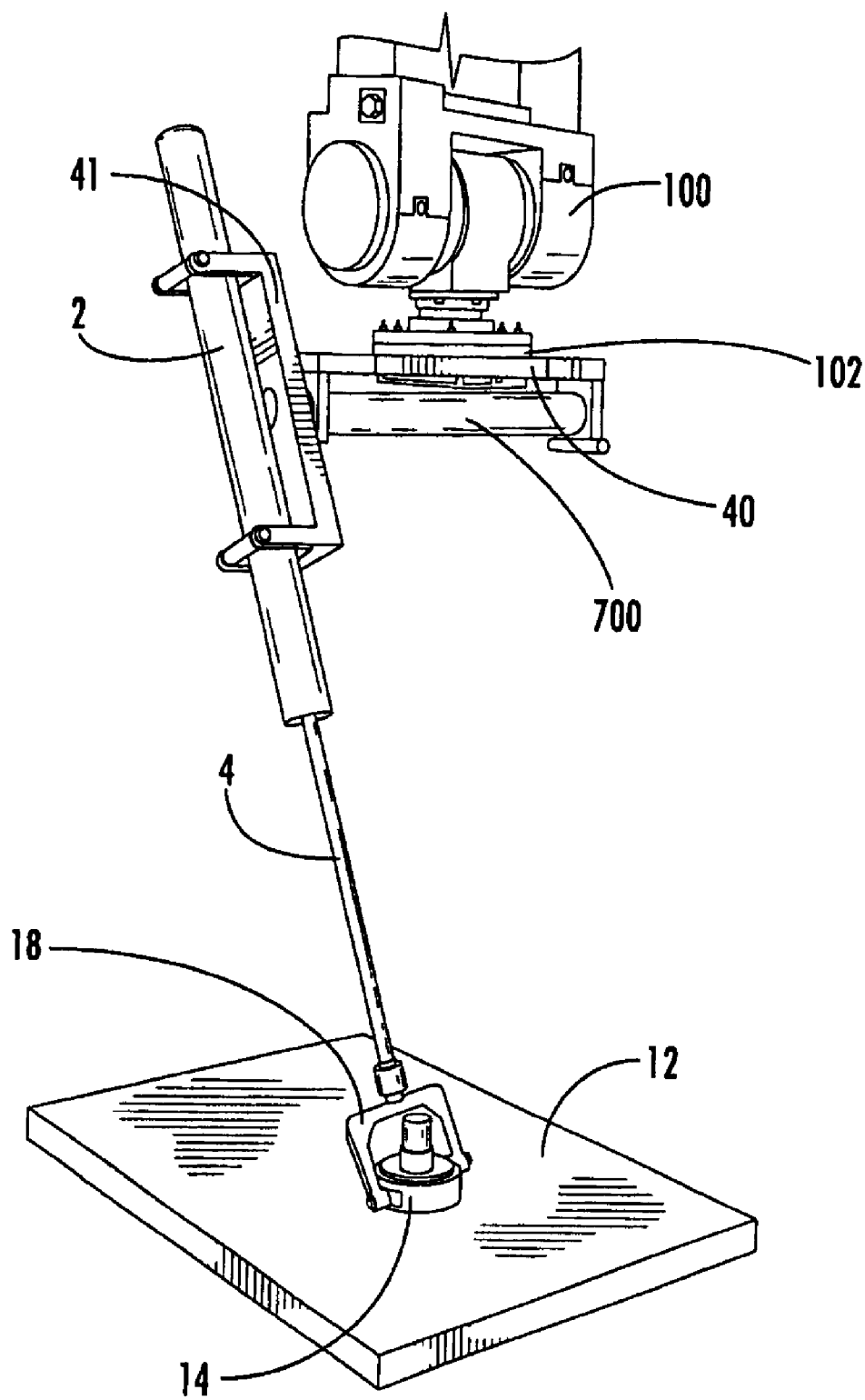
FIG. 7 is an overhead perspective view of an end effector of the present invention being used to scan a structure.
Figure 8:
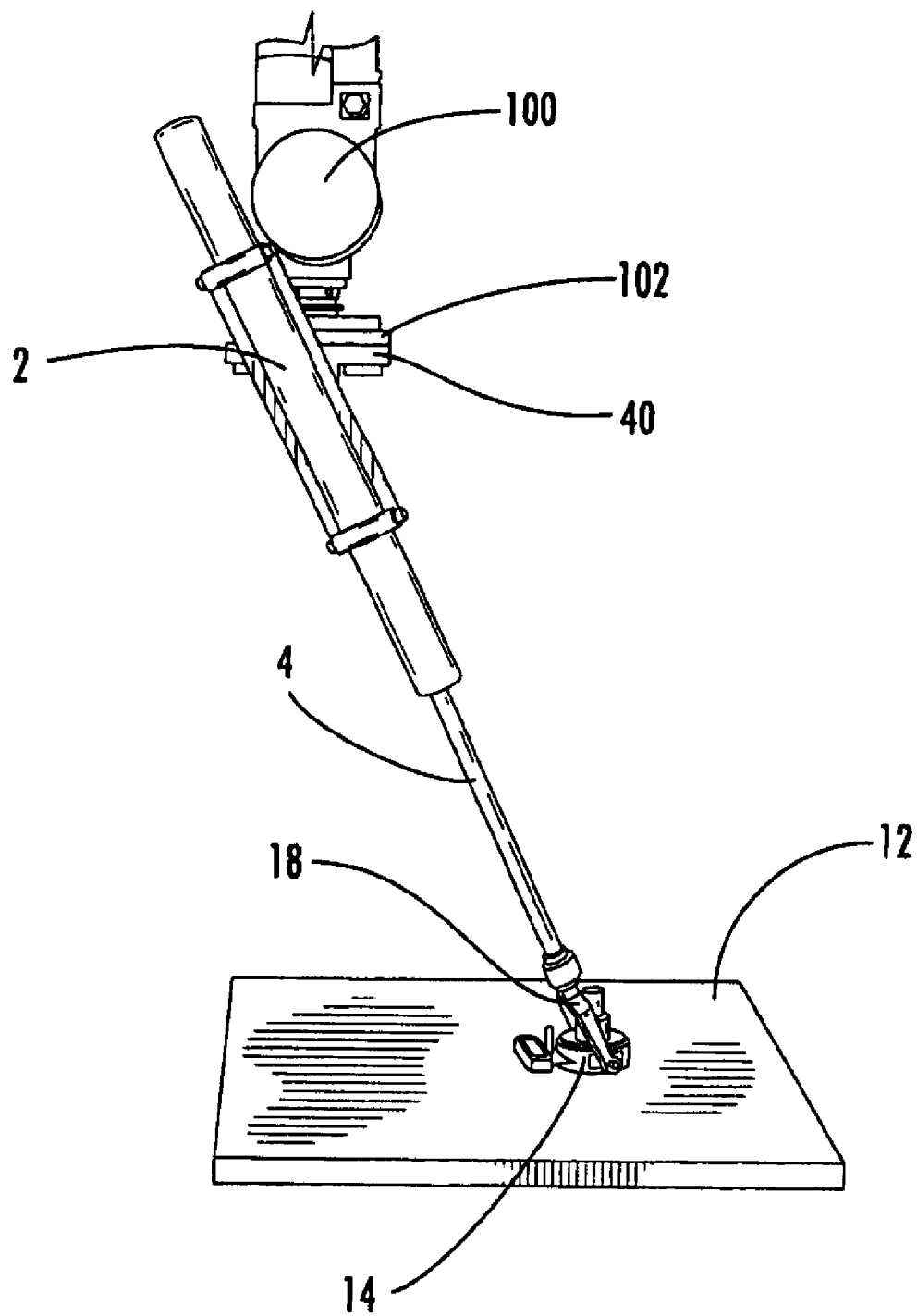
FIG. 8 is a side view of the end effector being used to scan the structure.

FIG. 7 is an overhead perspective view of an end effector of the present invention being used to scan a structure. FIG. 8 is a side view of the end effector being used to scan the structure. The end effector of FIGS. 7 and 8 include two tube sections, a tube 2 and a second access rotor tube 700, to permit increased orientation of the end effector. The second tube may also provide increased extension from a control bridge 100, such as where the second access rotor tube 700 also includes a telescoping arm to which the tube 2 connects. In the embodiment shown in FIGS. 7 and 8, a bridge base 102 of a control system bridge 100 magnetically couples to an attachment member 40 of a second axis rotor 700. The second axis rotor 700 is connected to a support mechanism 41 of tube 2. An arm 4 extends from tube 2 and attaches to an inspection probe 14 using a probe attachment 18. A second-axis rotor 700 may help to provide improved orientation for pressing and holding an inspection probe 14 against a structure 12 to be inspected.

An end effector according to the present invention provides for inspection of a greater variety of structures using a typical control system such as a robotic gantry system. The end effector and features of the end effector such as quick release clamps for adjusting the position of a tube, offset release clamps for releasing magnetic coupling of the end effector to a control bridge and tube extensions reduce set-up and change-out times for scanning structures. Magnetic coupling of an attachment member of an end effector of the present invention provides for breakaway capabilities. Cut-off switches on an attachment member or a control system bridge and on an arm or a tube provide emergency cut-off capabilities. A constant outward force to extend the arm from the tube allows for use of magnetically-coupled inspection probes by pushing and holding the magnetically coupled inspection probe against the surface of a part under inspection. In addition, traditional pulse-echo UT and other one-sided inspection techniques are capable of using end effectors according to embodiments of the present invention.

In operation a method of inspecting a structure using an end effector of the present invention may be performed by magnetically coupling a bridge of a control system to an attachment member of an end effector, coupling an inspection probe to the end effector, positioning the inspection probe against a surface of the structure, and controlling inspection of the structure with the control system. Positioning an inspection probe against a surface of the structure may be performed by telescoping the arm of the end effector to permit the inspection probe to contact the surface of the structure. For example, a constant force may be exerted upon the arm of the end effector to extend the arm from the tube in order to press an inspection probe against the surface of the structure. In operation, the magnetic coupling of the bridge and the attachment member may be released by separating the bridge and the attachment member, such as protruding an extension from an offset release clamp between the bridge and the attachment member.

Accordingly, provided is an end effector for inspecting a structure. An end effector includes a magnetically coupled attachment member for connecting the end effector to a control system bridge. An end effector also includes a telescoping arm at least partially disposed inside a tube. A force mechanism provides a force to extend the arm from the tube. A probe attachment, connected to the end of the arm opposite the tube, provides motion in at least one axis relative to the arm for an inspection probe attached to the end effector. Cut-off switches can be used to alert a control system to a separation of the end effector from the bridge and proximity of the bridge to a structure under inspection.

Many modifications and other embodiments of the inventions set forth will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed, they are used in a generic and descriptive sense only and not for purposes of limitation.

The invention claimed is:

1. An end effector comprising:
a telescoping arm;
a tube for receiving said telescoping arm, wherein said arm is at least partially disposed within said tube;
a force mechanism interoperably coupled to said arm and said tube for providing a force to dynamically extend said arm from said tube; and
an attachment member connected to said tube for magnetically attaching the end effector to another component by magnetic coupling and from which said telescoping arm extends, wherein said attachment member comprises at least one magnetic coupling mechanism selected from the group of a magnet and ferromagnetic material, and wherein said magnetic coupling mechanism is capable of cooperating with a magnetic coupling mechanism of said another component to create the magnetic coupling between said end effector and said another component, wherein said attachment member comprises at least one alignment member capable of providing alignment of said end effector with respect to at least one corresponding indentation of said another component for when said end effector is magnetically attached to said another component.

2. The end effector of claim 1, wherein said attachment member further comprises at least one releasable clamp for connecting said attachment member to said tube.

3. The end effector of claim 2, wherein said releasable clamp is capable of permitting adjustment of the position of said tube with respect to said attachment member by releasing said releasable clamp connecting said attachment member to said tube.

4. The end effector of claim 1, further comprising a detachable extension tube connected between said tube and said attachment member, wherein said detachable extension tube is capable of being detached from said tube and said attachment member and wherein said tube and said attachment member are capable of being connected without said detachable extension tube.

5. The end effector of claim 1, further comprising a cut-off switch, connected to at least one of said arm and said tube, to indicate when said arm is retracted into said tube beyond a predefined amount of retraction.

6. The end effector of claim 1, further comprising a cut off switch, connected to said attachment member, to indicate at least one of when said attachment member is separated from the another component and when said attachment member is connected to the another component.

7. The end effector of claim 1, wherein said arm is rotatably fixed with respect to said tube.

8. The end effector of claim 7, wherein said arm and said tube are formed with corresponding, non-circular cross-sectional shapes to prevent rotation, such that said arm is rotatably fixed with respect to said tube.

9. The end effector of claim 1, further comprising a releasable latch, connected to at least one of said arm and said tube, for affixing said arm within said tube in a retracted position.

10. The end effector of claim 9, further comprising a cut-off switch, connected to at least one of said arm and said tube, to indicate when said arm is retracted in to said tube beyond said releasable latch.

11. The end effector of claim 1, wherein said attachment member comprises at least one magnetic coupling offset release clamp.

12. The end effector of claim 11, wherein said magnetic coupling offset release clamp comprises at least one extension, wherein said extension is adapted to adjustably protrude from said attachment member.

13. The end effector of claim 1, wherein said force mechanism comprises a retractable metal spring.

14. The end effector of claim 1, further comprising bearings to support said arm in said tube, wherein said bearings are capable of permitting said arm to extend from and retract into said tube.

15. The end effector of claim 1, further comprising a probe attachment coupled to the distal end of said arm from said tube, wherein said probe attachment provides at least one axis of motion relative to said arm.

16. The end effector of claim 1, further comprising a second-axis rotor connected to said tube, wherein said attachment member connects to said second-axis rotor to connect to said tube.

17. An apparatus for inspection a structure comprising:
an end effector, comprising:
  a telescoping arm;
  a tube for receiving said telescoping arm, wherein said arm is at least partially disposed within said tube;
  a force mechanism interoperably coupled to said arm and said tube for providing a force to dynamically extend said arm from said tube; and
  an attachment member connected to said tube for magnetically attaching the end effector to another component by magnetic coupling and from which said telescoping arm extends, wherein said attachment member comprises at least one magnetic coupling mechanism selected from the group of a magnet and a ferromagnetic material, and wherein said magnetic coupling mechanism is capable of cooperating with a magnetic coupling mechanism of said another component to create the magnetic coupling between said end effector and said another component, wherein said attachment member comprises at least one alignment member capable of providing alignment of said end effector with respect to at least one corresponding indentation of said another component for when said end effector is magnetically attached to said another component; and
  an inspection probe connected to the distal end of said arm from said tube, wherein said end effector is capable of applying a force to said probe for pressing said probe against a surface of the structure.

18. The apparatus of claim 17, further comprising a control system comprising a bridge magnetically coupled to said attachment member, wherein said control system is capable of applying a force to said probe for moving said probe across the surface of the structure, and wherein said bridge is said another component.

19. The apparatus of claim 18, wherein said attachment member comprises at least one magnetic coupling offset release clamp.

20. The apparatus of claim 19, wherein said magnetic coupling offset release clamp comprises at least one extension, wherein said extension is adapted to adjustably protrude from said attachment member between said attachment member and said bridge.

21. The apparatus of claim 17, further comprising a cut-off switch, connected to at least one of said another component and said attachment member, for indicating at least one of when said another component and said attachment member are magnetically coupled and when said another component and said attachment member are separated.

22. The apparatus of claim 17, wherein said end effector further comprises a probe attachment coupled to the distal end of said arm from said tube for connecting said inspection probe to said arm, wherein said probe attachment provides at least one axis of motion for said inspection probe relative to said arm.

23. The apparatus of claim 17, wherein said end effector further comprises a second-axis rotor connected to said tube, wherein said attachment member connects to said second-axis rotor to connect to said tube.

24. A method of inspecting a structure comprising:
magnetically coupling a control system to an attachment member of an end effector;
coupling an inspection probe to the end effector, wherein the end effector comprises:
  a telescoping arm;
  a tube for receiving the telescoping arm, wherein the arm is at least partially disposed within the tube;
  a force mechanism interoperably coupled to the arm and the tube for providing a force to dynamically extend the arm from the tube; and
  an attachment member connected to the tube for magnetically attaching the end effector to the control system by magnetic coupling and from which the telescoping arm extends, wherein the attachment member comprises at least one magnetic coupling mechanism selected from the group of a magnet and ferromagnetic material, and wherein the magnetic coupling mechanism is capable of cooperating with a magnetic coupling mechanism of the control system to create the magnetic coupling between the end effector and the control system, wherein the attachment member comprises at least one alignment member capable of proving alignment of the end effector with respect to at least one corresponding indentation in the control system for when the end effector is magnetically attached to the control system, wherein the step of coupling an inspection probe comprises the step of aligning the end effector with respect to the control system by disposing the at least one alignment member into the at least one corresponding indentation in the control system for providing alignment of the end effector with respect to the at least one corresponding indentation in the control system for when the end effector is magnetically attached to the control system;
positioning the inspection probe against a surface of the structure; and
controlling inspection of the structure with the control system.

25. The method of claim 24, wherein the step of positioning the inspection probe comprises the step of telescoping an arm of the end effector to permit the inspection probe to contact the surface of the structure.

26. The method of claim 25, wherein the step of telescoping an arm of the end effector comprises the step of exerting a force by the force mechanism of the end effector upon the arm of the end effector, wherein the force is inclined to extend the arm from the tube.

27. The method of claim 24, further comprising the step of releasing the magnetic coupling of the control system and the attachment member by separating the control system and the attachment member.

28. The method of claim 27, wherein said step of releasing the magnetic coupling comprises the step of protruding an extension from at least one of the control system and the attachment member between the control system and the attachment member.

29. The method of claim 24, further comprising the step of separating the control system and the attachment member by manipulating at least one magnetic coupling offset release clamp, connected to at least one of the control system and the attachment member, configured for protruding an extension of the at least one magnetic coupling offset release clamp between the control system and the attachment member.

30. The method of claim 24, further comprising the step of securing at least one releasable clamp, connected to one of the attachment member and the tube, to connect the attachment member to the tube.

31. The method of claim 24, further comprising the step of connecting a detachable extension tube between the tube and the attachment member, wherein the detachable extension tube is capable of being unconnected from the tube and the attachment member and wherein the tube and the attachment member are capable of being connected without the detachable extension tube.

32. An end effector comprising,
a telescoping arm;
a tube for receiving said telescoping arm, wherein said arm is at least partially disposed within said tube;
a force mechanism interoperably coupled to said arm and said tube for providing a force to dynamically extend said arm from said tube; and
an attachment member connected to said tube for magnetically attaching the end effector to another component by magnetic coupling and from which said telescoping arm extends, wherein said attachment member comprises at least one magnetic coupling mechanism selected from the group of a magnet and ferromagnetic material, and wherein said magnetic coupling mechanism is capable of cooperating with a magnetic coupling mechanism of said another component to create the magnetic coupling between said end effector and said another component,
wherein said attachment member further comprises at least one releasable clamp for connecting said attachment member to said tube.

33. The end effector of claim 32, wherein said releasable clamp is capable of permitting adjustment of the position of said tube with respect to said attachment member by releasing said releasable clamp connecting said attachment member to said tube.

34. An end effector comprising,
a telescoping arm;
a tube for receiving said telescoping arm, wherein said arm is at least partially disposed within said tube;
a force mechanism interoperably coupled to said arm and said tube for providing a force to dynamically extend said arm from said tube;
an attachment member connected to said tube for magnetically attaching the end effector to another component by magnetic coupling and from which said telescoping arm extends, wherein said attachment member comprises at least one magnetic coupling mechanism selected from the group of a magnet and ferromagnetic material, and wherein said magnetic coupling mechanism is capable of cooperating with a magnetic coupling mechanism of said another component to create the magnetic coupling between said end effector and said another component, and
a detachable extension tube connected between said tube and said attachment member, wherein said detachable extension tube is capable of being detached from said tube and said attachment member and wherein said tube and said attachment member are capable of being connected without said detachable extension tube.

35. An end effector comprising,
a telescoping arm;
a tube for receiving said telescoping arm, wherein said arm is at least partially disposed within said tube;
a force mechanism interoperably coupled to said arm and said tube for providing a force to dynamically extend said arm from said tube; and
an attachment member connected to said tube for magnetically attaching the end effector to another component by magnetic coupling and from which said telescoping arm extends, wherein said attachment member comprises at least one magnetic coupling mechanism selected from the group of a magnet and ferromagnetic material, and wherein said magnetic coupling mechanism is capable of cooperating with a magnetic coupling mechanism of said another component to create the magnetic coupling between said end effector and said another component,
wherein said attachment member comprises at least one magnetic coupling offset release clamp.

36. The end effector of claim 35, wherein said magnetic coupling offset release clamp comprises at least one extension, wherein said extension is adapted to adjustably protrude from said attachment member.

* * * * *

UNITED STATES PATENT AND TRADEMARK OFFICE
CERTIFICATE OF CORRECTION

PATENT NO. : 7,114,406 B2 Page 1 of 1
APPLICATION NO. : 10/943045
DATED : October 3, 2006
INVENTOR(S) : Wright et al.

It is certified that error appears in the above-identified patent and that said Letters Patent is hereby corrected as shown below:

Column 14, Claim 24

Line 51, "proving" should read --providing--.

Signed and Sealed this

Twenty-seventh Day of February, 2007

JON W. DUDAS
*Director of the United States Patent and Trademark Office*